US008158581B2

(12) United States Patent
Glass et al.

(10) Patent No.: US 8,158,581 B2
(45) Date of Patent: *Apr. 17, 2012

(54) IGF-1 FUSION POLYPEPTIDES AND THERAPEUTIC USES THEREOF

(75) Inventors: David J. Glass, Cortlandt Manor, NY (US); George D. Yancopoulos, Yorktown Heights, NY (US); Thomas J. Daly, New City, NY (US); Nicholas J. Papadopoulos, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/894,278

(22) Filed: Sep. 30, 2010

(65) Prior Publication Data
US 2011/0020342 A1    Jan. 27, 2011

Related U.S. Application Data

(60) Continuation of application No. 12/134,301, filed on Jun. 6, 2008, now Pat. No. 7,837,999, which is a division of application No. 11/327,555, filed on Jan. 6, 2006, now Pat. No. 7,396,918.

(60) Provisional application No. 60/642,229, filed on Jan. 7, 2005, provisional application No. 60/656,583, filed on Feb. 25, 2005.

(51) Int. Cl.
*A61K 38/24* (2006.01)
*C07K 17/00* (2006.01)
*C07H 21/04* (2006.01)
*C12P 21/08* (2006.01)

(52) U.S. Cl. ...... 514/8.5; 530/350; 530/387.3; 530/399; 536/23.4

(58) Field of Classification Search .................. None
See application file for complete search history.

(56) References Cited

U.S. PATENT DOCUMENTS

| 5,473,051 A | 12/1995 | Altieri et al. |
| 5,473,054 A | 12/1995 | Jameson et al. |

FOREIGN PATENT DOCUMENTS

| EP | 0742228 | 11/1996 |
| WO | WO/90/15142 | 12/1990 |
| WO | 96/01275 A | 1/1996 |
| WO | 99/54359 A | 10/1999 |
| WO | 00/40613 A | 7/2000 |
| WO | 2005/033134 A | 4/2005 |

OTHER PUBLICATIONS

Bayne, 1988, Journal of Biological Chemistry, vol. 264, No. 19, pp. 11004-11008.*
Jansson et al., 1997, "Structural changes in insulin-like growth factor (IGF) I mutant proteins affecting binding kinetic rates to IGF binding protein 1 and IGF-I receptor."Biochemistry Apr. 8;36(14):4108-17.
Jansson et al., 1998, "The insulin-like growth factor (IGF)binding protein 1 binding epitope on IGF-I probed by heteronuclear NMR spectroscopy and mutational analysis."J Biol Chem. Sep. 18;273(38):24701-7.
Bayne et al., 1989, "The C region of human insulin-like growth factor (IGF) I is required for high affinity binding to the type 1 IGF receptor."J Biol Chem. Jul. 5;264(19):11004-8.
Heding et al., 1996, "Biosensor measurement of the binding of insulin-like growth factors I and II and their analogues to the insulin-like growth factor-binding protein-3."J Biol Chem. Jun. 14;271(24):13948-52.
Duguay, SJ, et al., "Processing of wild-type and mutant proinsulin-like growth factor-IA by subtilisin-related proprotein convertases." Journal of Biological Chemistry. (1997). 272(10): 6663-6670.
Duguay, SJ, et al., "Mutational analysis of the insulin-like growth factor I prohormone processing site." Journal of Biological Chemistry. (1995). 270(29): 17566-17574.
Samuelson, E, et al., "Enhanced in vitro refolding of insulin-like growth factor I using a solubilizing fusion partner." Biochemistry. (1994). 33(14): 4207-4211.
Shin, S-U, et al., "Functional Properties of Antibody Insulin-Like Growth Factor Fusion Proteins." Journal of Biological Chemistry. (1994). 269(7): 4979-4985.
Zhang, W, et al., "Positively charged side chains in the insulin-like growth factor-1 C- and D-regions determine receptor binding specificity." Journal of Biological Chemistry. (1994). 269(14): 10609-10613.
Dubaquie, et al., "Total Alanine-Scanning Mutagenesis of Insulin-like Growth Factor I (IGF-I) Identifies Differential Binding Epitopes for IGFBP-1 and IGFBP-3." Biochemistry. (1999). 38: 6386-6396.

* cited by examiner

*Primary Examiner* — Robert Landsman
*Assistant Examiner* — Ian Dang
(74) *Attorney, Agent, or Firm* — Valeta Gregg, Esq.; Izumi Yokoyama, Esq.

(57) ABSTRACT

A fusion protein comprising at least one IGF1 variant component and a fusion component (F), and, optionally, a signal sequence, exhibits improved stability relative to the native IGF1 or IGF2 polypeptide. The fusion component (F) may be a multimerizing component, such as an immunoglobulin domain, in particular, the Fc domain of IgG or a heavy chain of IgG. IGF1 variants were shown to have improved ability to increase muscle mass in a subject suffering from muscle atrophy caused by cachexia, immobilization, aging, chronic disease, cancer, hereditary condition, an atrophy-causing agent, and the like. IGF1 variants are also effective in decreasing blood glucose in a subject suffering from diabetes or hyperglycemia.

10 Claims, 1 Drawing Sheet

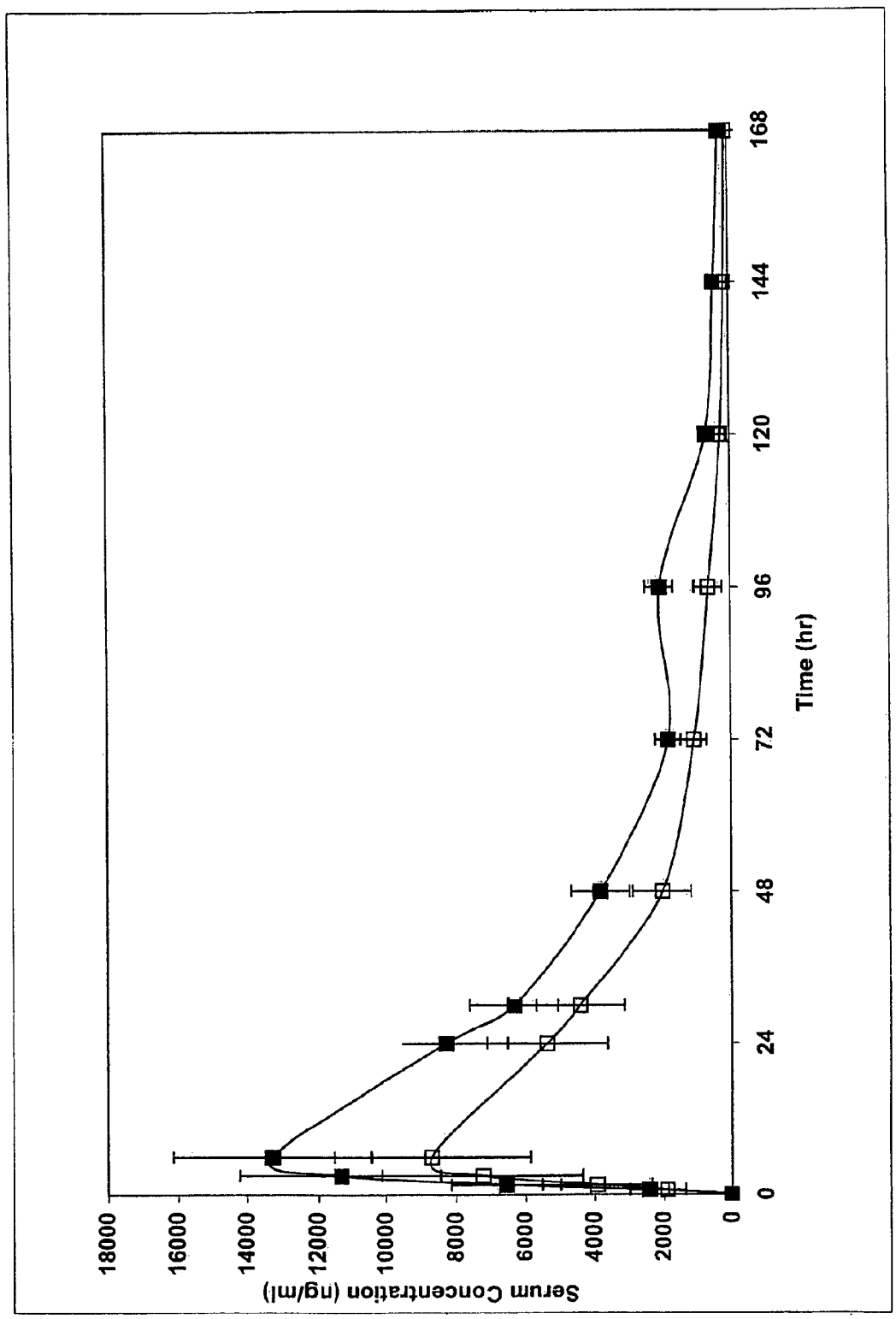

IGF-1 FUSION POLYPEPTIDES AND THERAPEUTIC USES THEREOF

CROSS-REFERENCE TO RELATED APPLICATIONS

This application is a continuation of U.S. patent application Ser. No. 12/134,301, filed 6 Jun. 2008, now U.S. Pat. No. 7,837,999, which is a divisional of U.S. patent application Ser. No. 11/327,555, filed 6 Jan. 2006, now U.S. Pat. No. 7,396,918, which claims the benefit under 35 USC §119(e) of U.S. Provisional Application Serial Nos. 60/642,229, filed 7 Jan. 2005, and 60/656,583, filed 25 Feb. 2005, which applications are herein specifically incorporated by reference in their entirety.

BACKGROUND

1. Field of the Invention

This invention relates to insulin-like growth factor 1 (IGF1) and insulin-like growth factor 2 (IGF2) polypeptides, methods of producing such polypeptides, and therapeutic methods for administering such polypeptides.

2. Description of Related Art

The insulin-like growth factors (IGFs) constitute a family of proteins having insulin-like and growth stimulating properties. The IGFs show close structural homology with proinsulin and elicit similar biological effects. Human IGF1 (also known as somatomedin C) is a 70 aa basic peptide (pI 8.4) having the protein and DNA sequences shown in SEQ ID NOs:1-2, and has a 43% homology with proinsulin (Rinderknecht et al. (1978) J. Biol. Chem. 253:2769-2776). Human IGF2 is a 67 amino acid basic peptide having the protein and DNA sequences shown in SEQ ID NOs:3-4. Specific binding proteins of high molecular weight having very high binding capacity for IGF1 and IGF2 act as carrier proteins or as modulators of IGF1 functions (Holly et al. (1989) J. Endocrinol. 122:611-618).

IGF1 and IGF2 and variants thereof have been used to treat humans suffering from growth hormone deficiencies, tissue wasting including burns, skeletal trauma, infection, cancer, cystic fibrosis, Duchenne muscular dystrophy, Becker dystrophy, autosomal recessive dystrophy, polymyositis, as well as myopathies and AIDS (U.S. Pat. No. 5,622,932).

BRIEF SUMMARY OF THE INVENTION

In the broadest embodiment, the present invention comprises compositions and methods providing IGF1 and IGF2 variant molecules to a subject in need thereof. More specifically, the present invention provides fusion polypeptides comprising a therapeutic IGF1 or IGF2 variants or analogs thereof fused to a fusion component (F). The fusion polypeptides of the invention are capable of remaining therapeutically active and available for a longer period of time than the naturally occurring molecule and resist inactivation by an IGF binding protein. The fusion polypeptides of the invention can also be used in a variety of in vitro and in vivo diagnostic and prognostic assays.

In a first aspect, the invention features an IGF1 fusion polypeptide, comprising (a) at least one IGF1 variant component, (b) a fusion component (F), and optionally, (c) a signal sequence, wherein the IGF variant component is the human IGF1 protein of SEQ ID NO:1 comprising (i) a modification of the C-terminus selected from the group consisting of deletion of 3 to 6 amino acids, e.g., 68-70 (Δ68-70), Δ67-70, Δ66-70, Δ65-70, deletion of Lys68(Δ68), substitution of amino acid 68 with another amino acid, deletion of amino acids 65-70 (Δ65-70), deletion of Lys65 (Δ65), and substitution of amino acid 65 with another amino acid; (ii) a modification of the N-terminus selected from the group consisting of deletion of amino acids 1-3 (Δ1-3) and substitution of Glu3 with a different amino acid, and/or (iii) a modification at Arg36 and/or Arg37 selected from the group consisting of deletion of Arg36 (Δ36), deletion of Arg 37 (Δ37), substitution of Arg36 with a different amino acid, e.g., Arg36Ala, and substitution of Arg37 with a different amino acid, e.g., Arg37Ala. In a specific embodiment, the IGF1 fusion protein has a deletion of amino acids 1-3 and Arg37 (2D-IGF1-Fc) (Δ1-3, ΔArg37). In another specific embodiment, the IGF1 fusion protein has a deletion of amino acids 1-3, Arg37 and amino acids 68-70 (3D-IGF1-Fc) (Δ1-3, ΔArg37, Δ68-70).

In a second aspect, the invention features an IGF2 fusion polypeptide, comprising (a) at least one IGF2 variant component, (b) a fusion component (F), and optionally, (c) a signal sequence, wherein the IGF variant component is the human IGF2 protein of SEQ ID NO:3 comprising (i) a modification of the C-terminus selected from the group consisting of deletion of 3 amino acids, e.g., 65-67 (Δ65-67), deletion of Lys65 (Δ65), and substitution of amino acid 65 with another amino acid; (ii) a modification of the N-terminus selected from the group consisting of deletion of amino acids 1-6 (Δ1-6) and substitution of Glu6 with a different amino acid, and/or (iii) a modification at Arg37 and/or Arg38 selected from the group consisting of deletion of Arg37 (Δ37), deletion of Arg 38 (Δ38), substitution of Arg37 with a different amino acid, e.g., Arg37Ala, and substitution of Arg38 with a different amino acid, e.g., Arg38Ala.

The fusion component (F) is any component that enhances the functionality of the fusion polypeptide. Thus, for example, an F may enhance the biological activity of the fusion polypeptide, aid in its production and/or recovery, or enhance a pharmacological property or the pharmacokinetic profile of the fusion polypeptide by, for example, enhancing its serum half-life, tissue penetrability, lack of immunogenicity, or stability. In a preferred embodiment, the fusion component allows the IGF variant component to evade serum binding proteins which may sequester IGF into a less biologically active compartment.

In preferred embodiments, F is a multimerizing component from the group consisting of (i) an amino acid sequence between 1 to about 500 amino acids in length, optionally comprising at least one cysteine residue, (ii) a leucine zipper, (iii) a helix loop motif, (iv) a coil-coil motif, and (v) an immunoglobulin domain. In some embodiments, the fusion component comprises an immunoglobulin-derived domain from, for example, human IgG, IgM or IgA. In specific embodiments, the immunoglobulin-derived domain is selected from the group consisting of the Fc domain and the heavy chain of IgG. The Fc domain of IgG may be selected from the isotypes IgG1, IgG2, IgG3, and IgG4, as well as any allotype within each isotype group.

In a specific embodiment, the invention features an IGF1 fusion polypeptide, comprising (i) an IGF1 variant component comprising the human IGF1 protein of SEQ ID NO:1 comprising deletion of amino acids 1-3 (Δ1-3 or delGPE), deletion of Arg36 (Δ36), and a deletion of 3-6 amino acids at the C-terminus (Δ68-70), (ii) an Fc domain of an IgG, and optionally, (iii) a signal sequence.

In another specific embodiment, the invention features an IGF2 fusion polypeptide, comprising (i) an IGF2 variant component comprising the human IGF2 protein of SEQ ID NO:3 comprising deletion of amino acids 1-6 (Δ1-6 or delAYRPSE), deletion of Arg37 (Δ37), and a deletion of 3 amino acids at the C-terminus (Δ65-67), (ii) an Fc domain of an IgG, and optionally, (iii) a signal sequence.

In other embodiments, the fusion component (F) is a targeting ligand, or derivative or fragment thereof, capable of binding specifically to a pre-selected cell surface protein, and thereby delivering said IGF1 or IGF2 to a target cell, e.g. a muscle cell. In specific embodiments, the targeting component is MuSK ligand, or a fragment of a MuSK ligand capable of binding the MuSK receptor. In specific embodiments, the MuSK-specific ligand is agrin or a fragment or derivative thereof capable of binding MuSK, or an anti-MuSK antibody or fragment or derivative thereof, including, for example, an scFv. In other specific embodiments, the muscle-targeting ligand of the muscle-targeting fusion polypeptide comprises three or more muscle cadherin (M-cadherin) extracellular cadherin domains, or derivatives or fragments thereof, capable of binding specifically to a muscle cells or other cells that express homophilic muscle cadherins. In one specific embodiment, the muscle-targeting ligand consists essentially of the first three (3) or four (4) N-terminal extracellular domains of M-cadherin.

In other embodiments, the fusion component (F) of the invention is another active compound, which may be any agent that is desirable to deliver to a pre-selected site for therapeutic purposes. In specific embodiments, the active or therapeutic agent is a ligand for a second cell surface receptor, and is capable of binding and activating a second receptor. In other embodiments, the active or therapeutic agent is an agent capable of blocking the activity of another agent that is active on the target cell. In a specific embodiment, the active or therapeutic agent is selected from the group consisting of IL-15, myotrophin, urocortin, urocortin II, a natural or mutant IGF1 or IGF2, insulin, the pro domain of myostatin, hGH, proliferin, follistatin, FSTL1, and FLRG, and a biologically active fragments thereof.

The polypeptide or fusion polypeptide of the invention may further optionally encode a signal sequence (SS) component. When a SS is part of the polypeptide, any SS known to the art may be used, including synthetic or natural sequences from any source, for example, from a secreted or membrane bound protein. Generally, a signal sequence is placed at the beginning or amino-terminus of the fusion polypeptide of the invention.

The components of the fusion polypeptides of the invention may be connected directly to each other or connected via one or more spacer sequences. In one preferred embodiment, the components are fused directly to each other. In another preferred embodiment, the components are connected with a spacer of 1-200 amino acids. Any spacer known to the art may be used to connect the polypeptide components. A spacer sequence may also include a sequence used to enhance expression of the fusion polypeptide, provide restriction sites, allow component domains to form optimal tertiary and quaternary structures and/or to enhance the interaction of a component with its receptor. In one embodiment, the fusion polypeptide of the invention comprises one or more peptide sequences between one or more components which is (are) between 1-25 amino acids.

The components of the fusion polypeptide of the invention may be arranged in a variety of configurations and may comprise more than one IGF variant polypeptide, for example, IGF-F; IGF-IGF-F; IGF-F-IGF; F-IGF; F-IGF-IGF, etc. However, when F is an Fc, the Fc must be on the C terminus of the fusion polypeptide. Similarly, in fusions comprising a second active component, such as human growth hormone (hGH), the configuration must be IGF variant-hGH.

In a second aspect, the invention features a nucleic acid encoding a fusion polypeptide of the invention.

In a third aspect, the invention features a vector comprising a nucleic acid molecule of the invention. In further fourth and fifth aspects, the invention encompasses vectors comprising the nucleic acid molecules of the invention, including expression vectors comprising the nucleic acid molecules operatively linked to an expression control sequence, and host-vector systems for the production of a fusion polypeptide which comprise the expression vector, in a suitable host cell; host-vector systems wherein the suitable host cell is, without limitation, a bacterial, yeast, insect, or mammalian cell. Examples of suitable cells include *E. coli, B. subtilis*, BHK, COS and CHO cells. Additionally encompassed are fusion polypeptides of the invention modified by acetylation or pegylation. Methods for acetylating or pegylating a protein are well known in the art.

In a related sixth aspect, the invention features a method of producing a fusion polypeptide of the invention, comprising culturing a host cell transfected with a vector comprising a nucleic acid molecule of the invention, under conditions suitable for expression of the protein from the host cell, and recovering the polypeptide so produced.

In a seventh aspect, the invention features therapeutic methods for the treatment of a disease or condition, comprising administering a therapeutically effective amount of the IGF fusion protein of the invention to a subject in need thereof, or a subject at risk for development of that disease or condition. When the disease or condition is a muscle condition, such as atrophy, the therapeutic method of the invention comprises administering a therapeutically effective amount of an IGF fusion protein of the invention to a subject in need thereof, wherein the muscle-related disease or condition is ameliorated or inhibited. The muscle-related condition or disorder treated by the fusion polypeptides of the invention may arise from a number of sources, including for example: denervation; degenerative, metabolic or inflammatory neuropathy; infantile and juvenile spinal muscular atrophies; autoimmune motor neuropathy; from chronic disease, including cachexia resulting from cancer, AIDS, fasting or rhabdomyolysis; and from muscular dystrophy syndromes such as Duchenne. The therapeutic method of the invention are useful to treat any condition which is results from an IGF deficiency or which may be improved by increased IGF levels, including dwarfism and heart disease, for example, improved heart tissue survival following myocardial infarction.

Accordingly, in an eighth aspect, the invention features pharmaceutical compositions comprising a fusion protein of the invention with a pharmaceutically acceptable carrier. Such pharmaceutical compositions may comprise the fusion proteins or nucleic acids which encode them, together with a pharmaceutically acceptable carrier.

Other objects and advantages will become apparent from a review of the ensuing detailed description.

BRIEF DESCRIPTION OF THE FIGURES

FIG. 1 is a graph showing the serum concentration of IGF1 variants 2D-IGF1-Fc (□) or 3D-IGF1-Fc (■) in CD-1 mice at 0, 24, 48, 72, 96, 120, 144 and 168 hrs (n=5 per group) (Mean±SEM).

DETAILED DESCRIPTION

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference.

General Description

The invention encompasses fusion polypeptides and nucleic acids that encode them which comprise one or more IGF variant components and a fusion component (F), which may comprise a multimerizing component, a targeting component, and/or one or more additional active or therapeutic agent(s).

Definitions

"Biologically active" fragments or derivatives of a component of the fusion polypeptides of the invention encompass any naturally occurring molecule, or mutant or derivative thereof capable of achieving the desired effect at the target site. For example, described herein are variants of IGF1, which have improved properties of activity and stability. The invention envisions the use of a mutant or derivative of the IGF1 molecules described herein which are capable of binding the IGF1 receptor. A "biologically active" fragment of derivative of any targeting component is any portion or mutant thereof capable of binding the target cell. Thus, for example, when the targeting ligand is agrin, a biologically active fragment or derivative is any portion or mutant of agrin capable of binding the MuSK receptor.

The terms "treatment", "treating", and the like are used herein to generally mean obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition. The population of subjects treated by the method of the disease includes subject suffering from the undesirable condition or disease, as well as subjects at risk for development of the condition or disease.

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

As used herein, a "condition or disease" generally encompasses a condition of a mammalian host, particularly a human host, which is undesirable and/or injurious to the host. Thus, treating a muscle-related condition with a fusion polypeptide which specifically targets skeletal muscle will encompass the treatment of a mammal, in particular, a human, who has symptoms reflective of decreased target muscle receptor activation, or who is expected to have such decreased levels in response to a disease, condition or treatment regimen. Treating a muscle-related condition or disease encompasses the treatment of a human subject wherein enhancing the activation of a target muscle receptor with the muscle specific fusion polypeptide of the invention results in amelioration of an undesirable symptom resulting from the muscle-related condition or disease. As used herein, a "muscle-related condition" also includes a condition in which it is desirable to alter, either transiently, or long-term, activation of a particular target muscle receptor.

IGF1 or IGF2 Variant Component

The first component of the polypeptides of the invention is an IGF1 or IGF2 variant ("IGF variant"). In the case of IGF1, such variants comprise mature human IGF1 (SEQ ID NO:1) having the following modifications: (i) a deletion of 3-6 amino acids at the C-terminus, e.g., Lys65 to Ala70; (ii) a modification at the N-terminus selected from the group consisting of deletion of amino acids 1-3 and substitution of Glu3 with a different amino acid, such as a alanine, valine, histidine or arginine, e.g., Glu3Arg or Glu3Ala, and/or (iii) a modification at Arg36 and/or Arg37 selected from the group consisting of deletion of Arg36, deletion of Arg 37, substitution of Arg36 with a different amino acid, e.g., Arg36Ala, and substitution of Arg37 with a different amino acid, e.g., Arg37Ala.

In the case of IGF2, such variants comprise the human IGF2 protein of SEQ ID NO:3 comprising (i) a modification of the C-terminus selected from the group consisting of deletion of 3 amino acids, e.g., 65-67 (Δ65-67), deletion of Lys65 (Δ65), and substitution of amino acid 65 with another amino acid; (ii) a modification of the N-terminus selected from the group consisting of deletion of amino acids 1-6 (Δ1-6) and substitution of Glu6 with a different amino acid, such as alanine, valine, histidine or arginine, e.g. Glu6Arg or Glu6Ala; and/or (iii) a modification at Arg37 and/or Arg38 selected from the group consisting of deletion of Arg37 (Δ37), deletion of Arg 38 (Δ38), substitution of Arg37 with a different amino acid, e.g., Arg37Ala, and substitution of Arg38 with a different amino acid, e.g., Arg38Ala.

Such modifications prevent the cleavage of the fusion component from the IGF1 or IGF2 variant, thus enhancing its stability and half-life.

Targeting Ligand Component

In some embodiments, the fusion component of the fusion polypeptides of the invention is a targeting ligand. A targeting ligand is a molecule, e.g., a protein or fragment thereof that specifically binds with high affinity to a target on a pre-selected cell, such as a surface protein such as a receptor that is present to a greater degree on the pre-selected cell target than on any other body tissue. For example, as described in U.S. Pat. Nos. 5,814,478 and 6,413,740, the MuSK receptor is highly specific to muscle. Accordingly, the cognate ligand agrin, as well as MuSK binding portions thereof is an example of a targeting ligand useful as a fusion component in the fusion polypeptides of the present invention. Another example of a targeting ligand is a group of cadherin domains from a human cadherin. Accordingly, human cadherin domains from, for example, human muscle cadherin may be used in the targeting fusion polypeptides of the invention to target muscle cells. The targeting ligand component of the fusion polypeptide of the invention may include a naturally occurring or engineered ligand, or a fragment thereof, capable of binding the pre-selected target cell.

In another embodiment of the invention, the targeting ligand component of the targeting fusion polypeptides of the invention consists of at least three, four or five muscle cadherin (M-cadherin) domains, or derivatives or fragments thereof, capable of binding specifically to target cells that express homophilic cadherins. (Shimoyama et al. (1998) J. Biol. Chem. 273(16): 10011-10018; Shibata et al. (1997) J. Biol. Chem. 272(8):5236-5270). In preferred embodiments, the fusion polypeptide of the invention comprises at least three cadherin domains from the extracellular domain of human M-cadherin (or biologically active fragments or derivatives thereof that are capable of binding homophilic M-cadherin), fused to the IGF1 variant component.

Further examples of targeting ligands also include, but are not limited to, antibodies and portions thereof that bind a pre-selected cells surface protein with high affinity. By "high affinity" is meant an equilibrium dissociation constant of at least $10^{-7}$ molar, as determined by assay methods known in the art, for example, BiaCore analysis. In one embodiment, the targeting ligand component of the targeting fusion polypeptides of the invention may also comprise one or more immunoglobulin binding domains isolated from antibodies generated against a selected tissue-specific surface protein or target tissue-specific receptor. The term "immunoglobulin or antibody" as used herein refers to a mammalian, including human, polypeptide comprising a framework region from an immunoglobulin gene or fragments thereof that specifically binds and recognizes an antigen, which, in the case of the present invention, is a tissue-specific surface protein, a target tissue-specific receptor, or portion thereof. If the intended targeting fusion polypeptide will be used as a mammalian therapeutic, immunoglobulin binding regions should be derived from the corresponding mammalian immunoglobulins. If the targeting fusion polypeptide is intended for non-therapeutic use, such as for diagnostics and ELISAs, the immunoglobulin binding regions may be derived from either human or non-human mammals, such as mice. The human immunoglobulin genes or gene fragments include the kappa, lambda, alpha, gamma, delta, epsilon, and mu constant regions, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Within each IgG class, there are different isotypes (e.g. $IgG_1$, $IgG_2$, etc.). Typically, the antigen-binding region of an antibody will be the most critical in determining specificity and affinity of binding.

An exemplary immunoglobulin (antibody) structural unit of human IgG, comprises a tetramer. Each tetramer is composed of two identical pairs of polypeptide chains, each pair having one light chain (about 25 kD) and one heavy chain (about 50-70 kD). The N-terminus of each chain defines a variable region of about 100-110 or more amino acids primarily responsible for antigen recognition. The terms "variable light chain" ($V_L$) and variable heavy chain ($V_H$) refer to these light and heavy chains respectively.

Antibodies exist as intact immunoglobulins, or as a number of well-characterized fragments produced by digestion with various peptidases. For example, pepsin digests an antibody below the disulfide linkages in the hinge region to produce $F(ab)'_2$, a dimer of Fab which itself is a light chain joined to $V_H$-$C_H$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region. While various antibody fragments are defined in terms of the digestion of an intact antibody, one of skill will appreciate that such fragments may be synthesized de novo either chemically or by using recombinant DNA methodology. Thus, the terms immunoglobulin or antibody, as used herein, also includes antibody fragments either produced by the modification of whole antibodies, or those synthesized de novo using recombinant DNA methodologies (e.g., single chain Fv) (scFv)) or those identified using phase display libraries (see, for example, McCafferty et al. (1990) Nature 348:552-554). In addition, the fusion polypeptides of the invention include the variable regions of the heavy ($V_H$) or the light ($V_L$) chains of immunoglobulins, as well as tissue-specific surface protein and target receptor-binding portions thereof. Methods for producing such variable regions are described in Reiter, et al. (1999) J. Mol. Biol. 290:685-698.

Methods for preparing antibodies are known to the art. See, for example, Kohler & Milstein (1975) Nature 256:495-497; Harlow & Lane (1988) Antibodies: a Laboratory Manual, Cold Spring Harbor Lab., Cold Spring Harbor, N.Y.). The genes encoding the heavy and light chains of an antibody of interest can be cloned from a cell, e.g., the genes encoding a monoclonal antibody can be cloned from a hybridoma and used to produce a recombinant monoclonal antibody. Gene libraries encoding heavy and light chains of monoclonal antibodies can also be made from hybridoma or plasma cells. Random combinations of the heavy and light chain gene products generate a large pool of antibodies with different antigenic specificity. Techniques for the production of single chain antibodies or recombinant antibodies (U.S. Pat. Nos. 4,946,778; 4,816,567) can be adapted to produce antibodies used in the fusion polypeptides and methods of the instant invention. Also, transgenic mice, or other organisms such as other mammals, may be used to express human or humanized antibodies. Alternatively, phage display technology can be used to identify antibodies, antibody fragments, such as variable domains, and heteromeric Fab fragments that specifically bind to selected antigens.

Screening and selection of preferred immunoglobulins (antibodies) can be conducted by a variety of methods known to the art. Initial screening for the presence of monoclonal antibodies specific to a tissue-specific or target receptor may be conducted through the use of ELISA-based methods or phage display, for example. A secondary screen is preferably conducted to identify and select a desired monoclonal antibody for use in construction of the tissue-specific fusion polypeptides of the invention. Secondary screening may be conducted with any suitable method known to the art. One preferred method, termed "Biosensor Modification-Assisted Profiling" ("BiaMAP") is described in US patent publication 2004/101920, allows rapid identification of hybridoma clones producing monoclonal antibodies with desired characteristics. More specifically, monoclonal antibodies are sorted into distinct epitope-related groups based on evaluation of antibody: antigen interactions.

Active or Therapeutic Agent

In some embodiments, the fusion component (F) of the polypeptides of the invention comprises a second active or therapeutic agent or mutant or derivative thereof, i.e. a molecule capable of having a desired effect when delivered to the pre-selected target site, e.g., cell or tissue. Active or therapeutic agents, include, but are not limited to, small molecules, hormones, growth factors, therapeutic biologics, activating antibodies and portions thereof, and blocking antibodies and portions thereof, that are capable of having a desirable effect upon delivery to a target cell or tissue.

In particular embodiments wherein the fusion polypeptide is directed at muscle cells or tissue, the fusion polypeptide comprises a second active or therapeutic agent that is active on muscle cells. Such agents include, but are not limited to, insulin, IL-15, myotrophin, urocortin, urocortin II, human myostatin propeptide, a natural or mutant IGF1 or IGF2, hGH, proliferin, follistatin, FSTL1, and FLRG, or mutants, derivative, or fragments thereof having biologically activity. In addition, the active or therapeutic agent may comprise a blocking antibody or biologically active derivative thereof, which blocks, for example, myostatin, activin receptor, BMP receptor 1, TNF receptor, IL-1 receptor, ALK3 receptor and ALK4 receptor. Alternatively, the active or therapeutic agent may comprise an activating antibody that activates, for example, the IFG1 receptor, B2adrenergic receptor or the IL-15 receptor complex.

Multimerizing Component in specific embodiments, the fusion component (f) of the fusion polypeptides of the invention comprises a multimerizing component. A multimerizing component includes any natural or synthetic sequence capable of interacting with another multimerizing component to form a higher order structure, e.g., a dimer, a trimer, etc. The multimerizing component may be selected from the group consisting of an amino acid sequence between 1 to about 500 amino acids in length, a leucine zipper, a helix loop motif, and a coil-coil motif. When the multimerizing component comprises an amino acid sequence between 1 to about 500 amino acids in length, the sequence may contain one or more cysteine residues capable of forming a disulfide bond with a corresponding cysteine residue on another fusion polypeptide comprising a multimerizing component with one or more cysteine residues. In some embodiments, the multimerizing component comprises an immunoglobulin-derived domain from, for example, human IgG, IgM or IgA, or comparable immunoglobulin domains from other animals, including, but not limited to, mice. In specific embodiments, the immunoglobulin-derived domain may be selected from the group consisting of the constant region of IgG, the Fc domain of IgG, an Fc-protein, and the heavy chain of IgG. The Fc domain of IgG may be selected from the isotypes IgG1, IgG2, IgG3, and IgG4, as well as any allotype within each isotype group.

Component Spacers

The components of the targeting fusion polypeptides of the invention may be connected directly to each other or be connected via spacers. The term "spacer" or "linker" means one or more molecules, e.g., nucleic acids or amino acids, or non-peptide moieties, such as polyethylene glycol, which may be inserted between one or more component domains. For example, spacer sequences may be used to provide a restriction site between components for ease of manipulation. A spacer may also be provided to enhance expression of the fusion polypeptide from a host cell, to decrease steric hindrance such that the component may assume its optimal tertiary or quaternary structure and/or interact appropriately with its target molecule. For spacers and methods of identifying desirable spacers, see, for example, George et al. (2003) Protein Engineering 15:871-879, herein specifically incorporated by reference.

A spacer sequence may include one or more amino acids naturally connected to a receptor component, or may be an added sequence used to enhance expression of the fusion protein, provide specifically desired sites of interest, allow component domains to form optimal tertiary structures and/or to enhance the interaction of a component with its target molecule. In one embodiment, the spacer comprises one or more peptide sequences between one or more components which is (are) between 1-100 amino acids, preferably 1-25. In one specific embodiment, the spacer is a three amino acid sequence; more specifically, the three amino acid sequence of Gly Pro Gly.

Nucleic Acid Construction and Expression

Individual components of the fusion polypeptides of the invention may be produced from nucleic acids molecules using molecular biological methods known to the art. The nucleic acid of SEQ ID NO:2 or SEQ ID NO:4 with the appropriate deletions or mutations may be used to prepare the IGF1 or IGF2 variants described herein. Such nucleic acid molecules are inserted into a vector that is able to express the fusion polypeptides when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion polypeptides of the invention under control of transcriptional/translational control signals. These methods may include in vitro recombinant DNA and synthetic techniques and in vivo recombinations (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

Expression of the nucleic acid molecules of the invention may be regulated by a second nucleic acid sequence so that the molecule is expressed in a host transformed with the recombinant DNA molecule. For example, expression of the nucleic acid molecules of the invention may be controlled by any promoter/enhancer element known in the art. Promoters which may be used to control expression of the fusion polypeptide molecules include, but are not limited to, the long terminal repeat as described in Squinto et al. (1991) Cell 65:1-20; the SV40 early promoter region, the CMV promoter, the M-MuLV 5' terminal repeat the promoter contained in the 3' long terminal repeat of Rous sarcoma virus, the herpes thymidine kinase promoter, the regulatory sequences of the metallothionine gene; prokaryotic expression vectors such as the b-lactamase promoter, or the tac promoter (see also "Useful proteins from recombinant bacteria" in Scientific American (1980) 242:74-94); promoter elements from yeast or fungi such as the Gal 4 promoter, the ADH (alcohol dehydrogenase) promoter, PGK (phosphoglycerol kinase) promoter, alkaline phosphatase promoter, and tissue-specific transcriptional control regions derived from elastase I gene, insulin gene, immunoglobulin gene, mouse mammary tumor virus, albumin gene, α-fetoprotein gene, α1-antitrypsin gene, β-globin gene, myelin basic protein gene, myosin light chain-2 gene, and gonadotropic releasing hormone gene.

The nucleic acid constructs of the invention are inserted into an expression vector or viral vector by methods known to the art, wherein the nucleic acid molecule is operatively linked to an expression control sequence. Also provided is a host-vector system for the production of a tissue-specific fusion polypeptide of the invention, which comprises the expression vector of the invention, which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS, CHO, 293, BHK or NS0 cell.

The invention further encompasses methods for producing the fusion polypeptides of the invention by growing cells transformed with an expression vector under conditions permitting production of the tissue-specific fusion polypeptides and recovery of the fusion polypeptides so produced. Cells may also be transduced with a recombinant virus comprising the nucleic acid construct of the invention.

The fusion polypeptides may be purified by any technique, which allows for the subsequent formation of a stable polypeptide. For example, and not by way of limitation, the fusion polypeptides may be recovered from cells either as soluble polypeptides or as inclusion bodies, from which they may be extracted quantitatively by 8M guanidinium hydrochloride and dialysis. In order to further purify the fusion polypeptides, conventional ion exchange chromatography, hydrophobic interaction chromatography, reverse phase chromatography or gel filtration may be used. The fusion polypeptides may also be recovered from conditioned media following secretion from eukaryotic or prokaryotic cells.

Therapeutic Methods

The invention herein further provides for the development of IGF fusion polypeptides described herein as a therapeutic for the treatment of patients suffering from disorders which may be ameliorated by providing IGF1 or IGF2, for example, a condition caused or worsened by an IGF deficiency. For example, a decrease in muscle mass, or atrophy, is associated with various physiological and pathological states. For example, muscle atrophy can result from denervation due to nerve trauma; degenerative, metabolic or inflammatory neuropathy, e.g. Guillian-Barré syndrome; peripheral neuropathy; or nerve damage caused by environmental toxins or drugs. Muscle atrophy may also result from denervation due to a motor neuropathy including, for example, adult motor neuron disease, such as Amyotrophic Lateral Sclerosis (ALS or Lou Gehrig's disease); infantile and juvenile spinal muscular atrophies; and autoimmune motor neuropathy with multifocal conductor block. Muscle atrophy may also result from chronic disease resulting from, for example, paralysis due to stroke or spinal cord injury; skeletal immobilization due to trauma, such as, for example, fracture, ligament or tendon injury, sprain or dislocation; or prolonged bed rest. Metabolic stress or nutritional insufficiency, which may also result in muscle atrophy, include the cachexia of cancer and other chronic illnesses including AIDS, fasting or rhabdomyolysis, and endocrine disorders such as disorders of the thyroid gland and diabetes. Muscle atrophy may also be due to muscular dystrophy syndromes such as Duchenne, Becker, myotonic, fascioscapulohumeral, Emery-Dreifuss, oculopharyngeal, scapulohumeral, limb girdle, and congenital types, as well as the dystrophy known as Hereditary Distal Myopathy. Muscle atrophy may also be due to a congenital myopathy, such as benign congenital hypotonia, central core disease, nemalene myopathy, and myotubular (centronuclear) myopathy. Muscle atrophy also occurs during the aging process. Muscle atrophy in various pathological states is associated with enhanced proteolysis and decreased production of muscle proteins.

The IGF1 and IGF2 fusion polypeptides of the invention are also useful in diseases associated with an IGF deficiency, such as dwarfism. Still further, IGFs have been shown to improve the survival of cardiac muscle cells after an event such as a myocardial infarction, thus the fusion polypeptides of the invention are useful in a subject who has experienced such an event.

The ability of the IGF fusion polypeptides of the invention to evade the large number of IGF-binding proteins present in a mammal makes them therapeutically useful for efficiently treating conditions which may benefit from an increased IGF level, such as recovery from atrophy-promoting conditions, situations in which skeletal muscle mass was decreasing, or situations in which muscle hypertrophy is desirable, such as during recovery from immobilization, aging, cancer, etc.

Because IGF receptors are expressed broadly, IGF fusion molecules of the invention wherein the fusion component is a multimerizing component such as Fc or another active component could further be used in settings other than muscle. For example, IGF1 and IGF2 have been shown to be bone growth factors, and therefore an IGF1-Fc or IGF2-Fc or an IGF1 or IGF2 fusion to growth hormone could be useful in the treatment of osteoporosis or other bone loss or weakness, including age related weakness, frailty or sarcopenia. The non-targeted molecules may also be useful in settings of more general body mass wasting—such as cachexia. Cachexia is a condition causing body mass loss, including, but not limited to, muscle mass. Settings of cachexia include cancer-induced cachexia, AIDS-induced cachexia, sepsis-induced cachexia, renal failure-induced cachexia, and congestive heart failure. Also, there is growth retardation in many settings, including thalassaemia, which causes short stature. Short stature in general would be a setting for an IGF1 or IGF2 fusion protein that is not targeted directly to muscle—such as the IGF1-Fc or IGF2-Fc or the IGF1-GH or IGF2-GH embodiments. An additional use for IGF1 or IGF2 is to complement or substitute for insulin. In settings of insulin-insensitive diabetes, IGF1 or IGF2 fusion proteins of the invention may be used. Such variants may further be used simply as a substitute for insulin in settings of hyperglycemia. Further additional uses for the IGF1 and IGF2 fusions described herein include use in the weaning of individuals from ventilators and for the treatment of conditions such as anemia wherein the proliferation of blood cells is desired.

Methods of Administration

Methods known in the art for the therapeutic delivery of agents such as proteins or nucleic acids can be used for the therapeutic delivery of an IGF fusion polypeptide or a nucleic acid encoding a IGF fusion polypeptide of the invention, e.g., cellular transfection, gene therapy, direct administration with a delivery vehicle or pharmaceutically acceptable carrier, indirect delivery by providing recombinant cells comprising a nucleic acid encoding an IGF fusion polypeptide of the invention.

Various delivery systems are known and can be used to administer the fusion polypeptide of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, pulmonary, intranasal, intraocular, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Cellular Transfection and Gene Therapy

The present invention encompasses the use of nucleic acids encoding the fusion polypeptides of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. The compositions are administered (e.g., by injection into a muscle) to a subject in an amount sufficient to elicit a therapeutic response.

In another aspect, the invention provides a method of treating a target site, i.e., a target cell or tissue, in a human or other animal comprising transfecting a cell with a nucleic acid encoding a tissue-specific fusion polypeptide of the invention, wherein the nucleic acid comprises an inducible promoter operably linked to the nucleic acid encoding the targeting fusion polypeptide. For gene therapy procedures in the treatment or prevention of human disease, see for example, Van Brunt (1998) Biotechnology 6:1149-1154.

Combination Therapies

In numerous embodiments, the fusion polypeptides of the present invention may be administered in combination with one or more additional compounds or therapies. For example, multiple fusion polypeptides can be co-administered in conjunction with one or more therapeutic compounds. The combination therapy may encompass simultaneous or alternating administration. In addition, the combination may encompass acute or chronic administration.

Pharmaceutical Compositions

The present invention also provides pharmaceutical compositions comprising a fusion protein of the invention and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the fusion polypeptide of the invention which will be effective in the treatment of a condition or disease can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally about 20-5000 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Kits

The invention also provides a pharmaceutical pack or kit comprising one or more containers filled with at least one fusion polypeptide or nucleic acid encoding a fusion polypeptide of the invention. The kits of the invention may be used in any applicable method, including, for example, diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Transgenic Animals

The invention includes transgenic non-human animals expressing an IGF fusion polypeptide of the invention. A transgenic animal can be produced by introducing nucleic acid into the male pronuclei of a fertilized oocyte, e.g., by microinjection, retroviral infection, and allowing the oocyte to develop in a pseudopregnant female foster animal. Any of the regulatory or other sequences useful in expression vectors can form part of the transgenic sequence. A tissue-specific regulatory sequence(s) can be operably linked to the transgene to direct expression of the transgene to particular cells. A transgenic non-human animal expressing a tissue-specific fusion polypeptide of the invention is useful in a variety of applications, including as a means of producing such fusion proteins. Further, the transgene may be placed under the control of an inducible promoter such that expression of the tissue-specific fusion polypeptide may be controlled by, for example, administration of a small molecule.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

IGF Fusion Polypeptides are Cleaved at Lys 65 or 68

A fusion polypeptide was constructed utilizing human IGF1 containing human IGF1 (Δ1-3, delR37) fused to human Fc. The polypeptide was purified and injected into mice. Blood samples were taken every 24 hours for seven days. Western analysis was conducted using an antibody specific to the human Fc. After three days, a lower-migrating band was noticed, indicating that the IGF1-Fc was being proteolytically cleaved in serum. More serum was taken, and this lower-migrating species was purified and sequenced. It was established that the IGF1-Fc construct was cleaved at the lysine 68 or the lysine 65 in the IGF1 variant. Based on this result, constructs are prepared in which the terminal three to six amino acids are removed, or the lysine at position 65 or 68 is mutated to another amino acid such as alanine or glycine. Such variants are utilized in preparation of fusion polypeptides of the invention comprising fusion components such as multimerizing components, targeting ligands, and other active compounds, and are found to have greater stability and half-life than comparable constructs with the lysine at position 65 or 68 of the IGF1 variant component.

Example 2

IGF1-Fc Fusion Polypeptides

Fusion polypeptide constructs were made using IGF1variant-Fc, or Fc-IGF1 variant, utilizing the variant IGF1 (Δ1-3, delR37) and human IgG derived Fc. The activity of IGF1 was measured by its ability to phosphorylate the IGF1 receptor and Akt kinase. Such phosphorylation was determined by a Western blot, using phospho-specific antibodies to the various molecules, or by immune-precipitating the receptors (such as IGFR), and Westerning with an antibody specific to anti-phospho-tyrosine. Such blots indicated active phosphorylation of Akt using the construct IGF1-Fc, but little or no activity utilizing the construct Fc-IGF1.

IGF1 (Δ1-3, delR37)-Fc was administered to SCID mice intra-peritoneally or subcutaneously via daily injections or via injections every other day. 4.5 mgs/kg of fusion protein were used for the injections. Control mice got no IGF1-Fc protein. A third group of mice received both 15 mg/kg dexamethosone subcutaneously per day. This dosage is sufficient to result in 15% loss of muscle mass after twelve days. A fourth group of mice received both the dexamethasone and the IGF1 (Δ1-3, delR37)-Fc. Mice in this fourth group experienced either no atrophy or statistically significant reductions in atrophy (5% atrophy in tibialis anterior (TA) muscle for mice which received both dexamethasone and IGF1 (Δ1-3, delR37)—vs 15% atrophy of TA for those mice which received only dexamethasone).

Example 3

IGF1-hGH Fusion Polypeptides

Fusion polypeptides were constructed utilizing IGF1 (Δ1-3, delR37) with hGH as the fusion component. In addition to measuring IGF1 activity, the activity of human growth hormone (hGH) was measured by its ability to phosphorylate Stat5. Surprisingly, constructs having the configuration IGF1variant-hGH caused phosphorylation of both IGF1 receptors and Stat5, while constructs with the configuration hGH-IGF1 variant had little or no activity.

Phosphorylation assays indicated that fusion proteins having the configuration IGF1 variant-hGH, which includes both hGH and the hIGF1 variant described above, is capable of simultaneously activating the IGF1 Receptor, Akt, and Stat5. Such phosphorylation was determined by a Western blot, using phospho-specific antibodies to the various molecules, or by immune-precipitating the receptors (such as IGFR), and Westerning with an antibody specific to anti-phospho-tyrosine. In addition, all of the above fusion polypeptides were made using human IGF1 mutants which had the first three amino acids deleted (Δ1-3) and either elimination or substitution of the arginines at positions 36 and/or 37. Such mutant IGF1 molecules demonstrated both resistance to cleavage as well as reduced binding by IGF-1 binding proteins (specifically IGF1 binding protein 5) without affecting signaling ability on C2C12 myotubes.

Fusion proteins comprising the IGF1 variants described above as well as deletion of amino acids 65-70 or 68-70 or mutation of the lysine at position 65 and 68 are constructed and tested for their ability to simultaneously activate the IGF1 Receptor, Akt, and Stat5, as determined by a Western blot, using phospho-specific antibodies to the various molecules, or by immune-precipitating the receptors (such as IGFR), and Westerning with an antibody specific to anti-phospho-tyrosine. In addition, C2C12 myotubes are contacted with the fusions and hypertrophy measured as compared to hypertrophy caused by either IGF1 alone or hGH alone. In constructs in which a targeting ligand, such as agrin, is used as a fusion component, activity may be measured by phosphorylation of the target receptor, such as MuSK (Glass et al. (1996) 85:513-523; Beguinot et al. (1988) Biochemistry. 27(9):3222-8).

Example 4

IGF2 Fusion Polypeptides

All of the above constructs are prepared utilizing the IGF2 protein or DNA as set forth in SEQ ID NOS:3-4. The lysine at position 65 of IGF2 is found to be involved in the cleavage of fusion proteins comprising the IGF2 variant, supporting use of IGF2 variants with deletions in the terminal 3 amino acids (65-67).

Example 5

Effect of 2D-IGF1-Fc (Δ1-3, ΔArg37) on Blood Glucose

C57/BL6 mice were used at 13 weeks of age (n=3 mice per group). Mice were fasted for four hours. Baseline and post-injection blood samples were collected from the tail vein and blood glucose measured by glucometer. Either insulin, IGF1 or IGF1-Fc were administered intraperitoneally and glucose was measured from blood collected from the tail vein 60 minutes after the administration of drug. Insulin was administered at 2 U/kg. IGF-I was used at a 10-fold higher dose than insulin (700 μg/Kg) based on comparative affinity of IGF-I for insulin receptor. 2D-IGF1-Fc (hIGFΔ1-3, ΔArg37) was administered at dose equimolar to that of IGF-I (3.5 mg/kg).

Results: Insulin caused a 66% decrease in blood glucose (207±5.5 mg/dl baseline vs. 70±22.2 mg/dl post-injection), IGF-I induced a 45% decrease in blood glucose (200±6.7 mg/dl baseline vs. 109±13.7 mg/dl post-injection), and 2D-IGF1-Fc caused a 30% blood glucose decrease (184±7.3 mg/dI baseline vs. 129±15.9 mg/dl post-injection). These results show that IGF1-Fc is effective in reducing blood gucose in fasted C57Bl/6 mice in an acute study.

Example 6

Pharmacokinetic Analysis of 2D-IGF1-Fc and 3D-IGF1-Fc

CD-1 mice (n=5 per group) were subcutaneously injected with 5 mg/kg of either human IGF1 derivative 2D-IGF1-Fc or 3D-IGF1-Fc (hIGF, Δ1-3, ΔArg37, Δ68-70). Serum samples were collected over a 7 day period and ELISA assays performed with an anti-human IGF1 (USB Cat. No. 17661-05) and detecting antibody goat anti-human IgG.Fc-HRP (Jackson Immuno Research Cat. No. 109-035-098). The results are shown in FIG. 1. Pharmacokinetic parameters are shown in Table 1.

TABLE 1

Pharmacokinetic Parameters

|  |  | 2D-IGF1-Fc | 3D-IGF1-Fc |
|---|---|---|---|
| $T_{max}$ | hr | 5.40 ± 1.12 | 6.00 ± 1.10 |
| $C_{max}$ | mcg/mL | 9.10 ± 1.75 | 13.27 ± 2.85 |
| $T_{1/2}$ | hr | 24.09 ± 4.41 | 29.85 ± 5.51 |
| AUC all | mcg*hr/mL | 325.42 ± 61.55 | 554.55 ± 112.23 |
| AUCINF (obs) | mcg*hr/mL | 328.31 ± 62.10 | 566.82 ± 114.63 |
| $V_Z$(obs)/F | mL/kg | 535.77 ± 101.88 | 395.78 ± 82.00 |
| CL(obs)/F | mL/hr/kg | 15.41 ± 2.91 | 9.26 ± 1.97 |
| MRT last | hr | 32.69 ± 6.00 | 42.80 ± 7.87 |
| MRTINF (obs) | hr | 34.19 ± 6.27 | 42.46 ± 7.80 |

Example 7

IGF1-Fc Molecules Induce Skeletal Muscle Hypertrophy In Vivo

2D-IGF1-Fc and 3D-IGF1-Fc were injected subcutaneously into adult 8-week old SCID mice daily at a dose of 1.6 mg/kg or with saline vehicle for 12 days (N=5 per group). At the end of the experiment, muscles (tibialis anterior and the gastrocnemius complex) were removed and the muscle wet weight measured. Injection of 2D-IGF1-Fc caused a 23.07±2.14% (mean±SEM) increase in tibialis anterior mass and a 17.00±2.07% increase in gastrocnemius mass compared to control muscles. Injection of 3D-IGF1-Fc caused a 9.45±3.72% increase in tibialis anterior mass and a 9.31±2.15% increase in gastrocnemius mass compared to control muscles.

Example 8

2D-IGF1-Fc is Superior to IGF-I in Inducing Skeletal Muscle Hypertrophy

The efficacy of 2D-IGF1-Fc in inducing skeletal muscle hypertrophy was also compared directly to unmodified IGF-I. Equimolar doses of each (4.8 mg/kg of 2D-IGF1-Fc or 0.93 mg/kg of IGF-I) or saline vehicle were injected subcutaneously into adult 8-week old SCID mice every other day for 12 days (N=5 per group). At the end of the experiment, muscles (tibialis anterior and the gastrocnemius complex) were removed and the muscle wet weight measured. Injection of 2D-IGF1-Fc caused a 13.35%±2.26 (mean±SEM) increase in tibialis anterior mass and a 9.39%±3.68% increase in gastrocnemius mass compared to control muscles. Injection of IGF-I gave 2.24%±2.27 increase in tibialis anterior mass and a 0.81%±1.51 increase in gastrocnemius mass compared to control muscles.

What is claimed is:

1. A fusion polypeptide comprising:
   (a) an insulin-like growth factor 1 (IGF1) variant polypeptide component comprising a human IGF1 protein of SEQ ID NO:1 with deletions of amino acid residues 1-3, 37, and 68-70; and
   (b) a fusion component (F), wherein F is an Fc domain or a heavy chain of human IgG,
   wherein the IGF1 variant polypeptide component retains the functional activity of IGF1.

2. A dimer of the fusion polypeptide of claim 1.

3. The fusion polypeptide of claim 1, wherein the IGF1 component and the F component are connected via a spacer sequence.

4. A nucleic acid encoding the fusion polypeptide of claim 1.

5. An expression vector comprising the nucleic acid of claim 4.

6. An isolated host cell comprising the expression vector of claim 5.

7. The host cell of claim 6 being a bacterial, yeast, insect, or mammalian cell.

8. The host cell of claim 7, wherein the bacterial cell is an *E. coli*, and the mammalian cell is a CHO cell.

9. A method of producing a fusion polypeptide, comprising culturing the host cell of claim 6, under conditions suitable for expression of the fusion polypeptide from the host cell, and recovering the polypeptide so produced.

10. A pharmaceutical composition comprising the fusion polypeptide of claim 1 and a pharmaceutically acceptable carrier.

* * * * *

SEQUENCE LISTING

<160> NUMBER OF SEQ ID NOS: 4

<210> SEQ ID NO 1
<211> LENGTH: 70
<212> TYPE: PRT
<213> ORGANISM: Homo Sapien

<400> SEQUENCE: 1

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
            20                  25                  30

```
Ser Ser Ser Arg Arg Ala Pro Gln Thr Gly Ile Val Asp Glu Cys Cys
            35                  40                  45

Phe Arg Ser Cys Asp Leu Arg Leu Glu Met Tyr Cys Ala Pro Leu
 50                  55                  60

Lys Pro Ala Lys Ser Ala
 65                  70

<210> SEQ ID NO 2
<211> LENGTH: 210
<212> TYPE: DNA
<213> ORGANISM: Homo Sapien

<400> SEQUENCE: 2
ggaccggaga cgctctgcgg ggctgagctg gtggatgctc ttcagttcgt gtgtggagac      60
aggggctttt atttcaacaa gcccacaggg tatggctcca gcagtcggag ggcgcctcag     120
acaggtatcg tggatgagtg ctgcttccgg agctgtgatc taaggaggct ggagatgtat     180
tgcgcacccc tcaagcctgc caagtcagct                                      210

<210> SEQ ID NO 3
<211> LENGTH: 67
<212> TYPE: PRT
<213> ORGANISM: Homo Sapien

<400> SEQUENCE: 3

Ala Tyr Arg Pro Ser Glu Thr Leu Cys Gly Gly Glu Leu Val Asp Thr
 1               5                  10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
            35                  40                  45

Arg Ser Cys Asp Leu Ala Leu Leu Glu Thr Tyr Cys Ala Thr Pro Ala
 50                  55                  60

Lys Ser Glu
 65

<210> SEQ ID NO 4
<211> LENGTH: 201
<212> TYPE: DNA
<213> ORGANISM: Homo Sapien

<400> SEQUENCE: 4
gcttaccgcc ccagtgagac cctgtgcggc ggggagctgg tggacaccct ccagttcgtc      60
tgtggggacc gcggcttcta cttcagcagg cccgcaagcc gtgtgagccg tcgcagccgt     120
ggcatcgttg aggagtgctg tttccgcagc tgtgacctgg ccctcctgga gacgtactgt     180 gctaccccg ccaagtccga g                                                201
```